(12) United States Patent
Maitre et al.

(10) Patent No.: US 10,048,515 B2
(45) Date of Patent: Aug. 14, 2018

(54) OPHTHALMIC ANTI-SOMNOLENCE LENS, DEVICE AND METHOD

(71) Applicant: Essilor International (Compagnie Generale d'Optique), Charenton-le-Pont (FR)

(72) Inventors: Nicolas Maitre, Charenton-le-Pont (FR); Delphine Passard, Charenton-le-Pont (FR); Melanie Tessieres, Charenton-le-Pont (FR)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 293 days.

(21) Appl. No.: 14/964,619

(22) Filed: Dec. 10, 2015

(65) Prior Publication Data

US 2016/0187673 A1 Jun. 30, 2016

(30) Foreign Application Priority Data

Dec. 30, 2014 (EP) .................................. 14307204

(51) Int. Cl.
| | |
|---|---|
| *G02C 11/04* | (2006.01) |
| *G02C 13/00* | (2006.01) |
| *G02C 7/10* | (2006.01) |
| *G02B 5/28* | (2006.01) |
| *A61M 21/00* | (2006.01) |

(52) U.S. Cl.
CPC ............... *G02C 11/04* (2013.01); *G02B 5/28* (2013.01); *G02C 7/104* (2013.01); *G02C 7/107* (2013.01); *G02C 7/108* (2013.01); *G02C 13/003* (2013.01); *A61M 2021/0044* (2013.01); *A61M 2021/0083* (2013.01); *G02C 2202/16* (2013.01)

(58) Field of Classification Search
CPC ........ G02C 11/04; G02C 7/104; G02C 7/107; G02C 7/108; G02C 13/003; G02C 2202/16; G02B 5/28; A61M 2021/0044; A61M 2021/0083
USPC ....................................................... 351/158
See application file for complete search history.

(56) References Cited

U.S. PATENT DOCUMENTS

| | | | |
|---|---|---|---|
| 2012/0215291 A1 | 8/2012 | Pugh et al. | |
| 2013/0278887 A1 | 10/2013 | Legerton | |
| 2014/0327967 A1 | 11/2014 | Blair et al. | |
| 2015/0146161 A1* | 5/2015 | Rigato ................. | G02B 1/115 351/159.6 |

FOREIGN PATENT DOCUMENTS

| | | |
|---|---|---|
| BE | 1018173 | 6/2010 |
| CN | 103338817 A | 10/2013 |

(Continued)

OTHER PUBLICATIONS

Extended European Search Report dated Sep. 4, 2015; Application No. 14307204.9.

*Primary Examiner* — William R Alexander
*Assistant Examiner* — Grant Gagnon
(74) *Attorney, Agent, or Firm* — Young & Thompson (57) ABSTRACT

The ophthalmic lens includes a substrate, the substrate having a rear face and a front face, and at least one external interferential coating, the at least one interferential coating being such that it enables to selectively reflect light arriving on the rear face with a local maximum of reflection of at least 10% for a wavelength within the range between 450 nm and 490 nm.

20 Claims, 3 Drawing Sheets

(56) References Cited

FOREIGN PATENT DOCUMENTS

| EP | 2816379 | 12/2014 |
|----|---------|---------|
| FR | 2822964 | 10/2002 |
| WO | 2012106542 | 8/2012 |

* cited by examiner

OPHTHALMIC ANTI-SOMNOLENCE LENS, DEVICE AND METHOD

The present invention relates to optical and ophthalmic systems, such as ophthalmic lenses, provided with interferential coatings. More particularly, the present invention relates to ophthalmic lenses having added value.

In the present invention, an ophthalmic lens is an optical element disposed near the eye of a wearer and aims at correcting wearer's vision, protecting wearer's eyes and/or enhance wearer's vision. Non limiting examples of ophthalmic lenses include non-corrective (also called plano or afocal lens) and corrective lenses, including single vision or multi-vision lenses like bifocal, trifocal or progressive lenses, which may be either segmented or non-segmented, including magnifying lenses and protective lenses or visors such as found in spectacles, glasses, goggles, and helmets. The optical article of the present invention is preferably a lens, and more preferably an ophthalmic lens such as a finished lens.

BACKGROUND OF THE INVENTION

The prevention of somnolence when driving a vehicle is an important issue of road traffic safety. Different devices and methods are known allowing to prevent the vehicle driver from getting sleepy or closing his eyes. For the treatment of somnolence, one often uses the perturbation of the circadian rhythm of sleep.

It is known that an illuminance of 20 lux with blue light, having a wavelength centered on approximately 470 nm, perturbs the circadian rhythm of sleep. Blue light is thus often used to prevent somnolence when driving (see, for example, J. Taillard et al., "*In-Car Nocturnal Blue Light Exposure Improves Motorway Driving: A Randomized Controlled Trial*", PLoS ONE 7(10), 2012).

Anti-somnolence devices using blue light are optoelectronic devices consisting of arrays of blue light emitting diodes. These devices may be arranged within the vehicle in order to illuminate it and thus also the driver while driving. They may also be fixed to the frame of the driver's glasses in front of the glasses in order to irradiate directly into the driver's eyes.

However, such devices suffer from some drawbacks. For example, a device illuminating the entire vehicle cabin may affect the comfort and well-being of the driver himself and passengers. When irradiated directly into the eyes, the driver may be blinded by the blue light. Thus, both solutions may not be appropriate to enhance road traffic safety.

According to the foregoing, there exists a need for an improved ophthalmic system to counteract somnolence of a vehicle driver and that resolves the cited problems.

SUMMARY OF THE INVENTION

According to a first aspect of the present invention, there is provided an ophthalmic lens comprising a substrate, the substrate having a rear face and a front face, the rear face being destined to face the eye of a user, and at least one external interferential coating on at least one face, the at least one interferential coating being such that it enables to selectively reflect light arriving on the rear face with a local maximum of reflection of at least 10% for a wavelength within the range comprised between 450 nm and 490 nm included, preferably for any wavelength between said range 450-490 nm.

The ophthalmic lens according to the first aspect is adapted to reflect blue light having the appropriate wavelength in the direction of a user's or wearer's eyes thanks to the coating, i.e., in the range 450-490 nm included and centered around 470 nm. Therefore, the blue light irradiating the user's eyes, his circadian rhythm of sleep is perturbed, thereby helping the user to stay awake, for example while driving his vehicle. It is to be noted that the invention may be of use to any user needing to fight-off sleep, such as for example night-shift workers, tired people using computers, or travellers with jet-lag.

According to an embodiment, the mean reflection for light in the range between 400 nm and 420 nm is less than 10%, preferably less than 7%, preferably less than 4%.

According to another embodiment, the mean reflection for light in the range between 420 nm and 440 nm is less than 10%, preferably less than 7%, preferably less than 4%.

Therefore, the reflection of undesired wavelengths is minimized. For example, wavelengths around 420-450 nm are considered phototoxic. The exposition of the user to these wavelengths is thus restricted by comparison to the amount of reflection of light in the 450 nm-490 nm range.

Preferably, the mean reflection for light in the range between 500 nm and 600 nm is less than 10%, preferably less than 7%.

Further, a reflection spectrum of the coating according to the invention comprises a peak centered inside the 450 nm-490 nm range, having a full width at half maximum (FWHM) smaller or equal to 100 nm, preferably smaller or equal to 80 nm, preferably smaller or equal to 60 nm.

The coating can thus combine the function of a partial optical mirror for light of wavelength within the 450 nm-490 nm with that of an anti-reflection (AR) coating for at least some parts of the visual spectrum out of the 450 nm-490 nm range.

Advantageously, the local maximum of reflection within the range of wavelengths comprised between 450 nm and 490 nm has a reflection value of at least two times greater, preferably four times greater, than the reflection value of light of wavelength 430 nm and/or of light of wavelength 500 nm.

In some embodiments, the coating comprises an interferential coating, said interferential coating comprising layers of high refractive index, HI, and layers of low refractive index, LI, said layers each having a thickness within the range of 1 nm to 500 nm. It is to be noted that the basic structure of the interferential coating can be similar to the one of an antireflective coating usually used in ophthalmics.

The multi-layered interferential coating of the invention comprises a stack of at least one layer with a high refractive index and of at least one layer with a low refractive index.

More preferably, the interferential coating comprises at least two layers having a refractive index higher than 1.6 (HI) and at least two layers having a refractive index lower than 1.55 (LI). It is here a simple stack, since the total number of layers in the interferential coating is higher than or equal to 3, preferably higher than or equal to 4, and lower than or equal to 15, more preferably lower than or equal to 10, and most preferably comprising from 6 layers to 9 layers.

Unless stated otherwise, all thicknesses disclosed in the present application relate to physical deposited thicknesses.

HI layers and LI layers don't need to alternate with each other in the stack, although they usually do. Two HI layers (or more) may be deposited onto each other, as well as two LI layers (or more) may be deposited onto each other. Such doubling of LI or HI layers may be applied to use two HI (or LI) layers of slightly different index.

In the present application, a layer of the interferential coating is said to be a layer with a high refractive index (HI) when its refractive index is higher than or equal to 1.6, preferably higher than or equal to 1.7, even more preferably higher than or equal to 1.8 and in particular may be higher than or equal to 1.9. A layer of an interferential coating is said to be a low refractive index layer (LI) when its refractive index is lower than 1.60, preferably lower than or equal to 1.50, more preferably lower than or equal to 1.47.

Unless otherwise specified, the refractive indexes referred to in the present application are expressed as measured at 25° C. at a wavelength of 550 nm.

The HI layer is a traditional high refractive index layer, which is well known in the art. It generally comprises one or more metal oxides such as, without limitation, zirconia ($ZrO_2$), titanium dioxide ($TiO_2$), alumina ($Al_2O_3$), tantalum pentoxide ($Ta_2O_5$), neodymium pentoxide ($Nd_2O_5$), praseodymium oxide ($Pr_2O_3$), praseodymium titanate oxide ($PrTiO_3$), lanthanum oxide ($La2O_3$), niobium oxide ($Nb_2O_5$), yttrium oxide ($Y_2O_3$). Optionally, the HI layers may further contain silica or other materials with a low refractive index, provided they have a refractive index higher than or equal to 1.6 as indicated hereabove. The preferred materials include $Ta_2O_5$, $TiO_2$, $PrTiO_3$, $ZrO_2$, $Al_2O_3$, $Y_2O_3$, and mixtures thereof.

The LI layers are also well known and may comprise, without limitation, silicon oxides, such as silica ($SiO_2$), magnesium fluoride ($MgF_2$), $ZrF_4AlF_3$, chiolite ($Na_3[Al_3F_{14}]$), cryolite ($Na_3[AlF_6]$), and their combinations, combined possibly with higher index material in small amounts such as alumina ($Al_2O_3$) or fluorine, preferably $SiO_2$ or $SiO_2$ doped with alumina. The LI layer is preferably a layer comprising at least 80% by weight of silica, more preferably at least 90% by weight of silica, relative to the layer total weight, and even more preferably consists in a silica layer.

The interferential coating outer layer is preferably a LI layer, preferably a silicone-oxide-based layer, comprising preferably at least 80% by weight of $SiO_2$, more preferably at least 90% by weight of silica (for example, a silica layer doped with alumina or with silicon or with oxygen), relative to the layer total weight, and even more preferably consists in a silica layer.

Generally, the HI layers have a physical thickness ranging from 5 to 600 nm, and the LI layers have a physical thickness ranging from 5 to 600 nm.

Generally, the antireflective coating total thickness is lower than 3 µm, preferably lower than or equal to 1 µm.

In one embodiment, the coating is on the rear face of the lens.

In one embodiment, the coating is not present on the entire surface of the face of the lens it is on. For example, in this embodiment, the interferential coating of the invention is not present inside of a working optical zone of the lens, more preferentially is present essentially on the temporal zone of the lens; the working optical zone being as defined below. Thus, in a variant of this embodiment, the rear face of the lens may bear, on the surface not covered by the interferential coating of the invention, a regular antireflective coating, or even an antireflective coating which even has low UV reflection.

Such design may be obtained through use of mask during a vacuum deposition process. Such design enables better vision, more clarity, and improved esthetics to the user.

According to a second aspect, there is provided an optical device comprising an ophthalmic lens according to the first aspect and a frame for supporting the ophthalmic lens in front of a wearer's eye, further comprising a light source attached to the frame, the light source being positioned and oriented for emitting a light toward the coating, such that the light does not illuminate directly the eye and such that the light emitted by the light source is reflected at least partially by the coating toward the eye.

The lens comprises a working optical zone, defined as being an area of a statistical distribution of a set of points on the lens through which passes the viewing direction of the individual during a particular task of vision or for use at a predetermined distance working, called intersection points. The wear area can be defined equivalently either spatially by a statistical distribution of points on the ophthalmic lens or on another projection plane linked to the ophthalmic lens or on the surface projected by the lens on the corresponding frame or, alternatively, vectorially by a statistical distribution of directions of gaze of the viewer. Alternatively, a simplified working optical zone can also be defined in tabulated way by a statistical distribution of lowered gaze angles in the plane sagittal of the individual.

The working optical zone, or pattern of usage, of the lens surface can be, for example, represented by a surface defined by the position of the barycentre BU of all measured points VP, the shape of this surface, for example circular, or elliptic, or nondescript, the spatial extent in one or two spatial dimensions along an X axis and/or an Y axis (depending on the horizontal and/or vertical standard deviation), and/or by some limits: high vertical limits, low vertical limits, nasal limits, and temporal limits.

By way of non-limiting example, the surface of the working optical zone of the lens is represented by an ellipse containing a predetermined percentage of the measured point of intersection, preferably 80% or 90% or 95% of the intersection points.

While the working optical zone highly depends on the user's visual behavior, the working optical zone is generally greater than a circle of radius 7 mm, centered on the optical center of the lens, and rarely extends out of a circle of 18 mm, centered on the optical center of the lens.

Accordingly, in general, the working optical zone is represented as a circle or ellipse centered on the optical center of the lens and of radius comprised between 7 mm and 18 mm.

According to an embodiment, the light source is positioned and oriented for having an illumination area outside the working optical zone of the lens surface.

The illumination area is defined as a zone which represents an area receiving 40%, preferably 60%, more preferably 80%, of the intensity of the light emitted by the light source as it intersects the lens surface, i.e. as it intersects a surface of the optical lens on the rear face of the substrate. In one example, the illumination area is considered as centered on the point which receives the most intensity.

In an embodiment, the illumination area intersects with less than half, preferably less than a quarter of the working optical zone.

In an embodiment, the illumination area does not reach closer than 7 mm from the optical center. In other words, the illumination area does not intersect with a circle of radius 7 mm centered on the optical center.

In one embodiment, the coating of the invention is not present in a part of the working optical zone. The interferential coating of the invention may, for example, be absent from all or part of a circle or ellipse of radius comprised between 7 mm included and 18 mm included centered on the optical center of the lens.

Alternatively, the coating of the invention is present on the whole lens.

In particular, when the coating of the invention is replaced by an antireflective stack in a part of the working optical zone, it is easier to position the illumination area. Indeed, even if the illumination area intersects with the working optical zone, the part that comprises an antireflective stack will not reflect much light toward the eyes of the wearer. This thus limits risk of dazzling by light reflected from the working optical zone.

Preferably, the light source emitting with a spectrum with a maximum of emission for a wavelength within the range of 460 nm to 480 nm, emits at least four times the amount of light at wavelength of the local maximum of emission as compared to light emitted at wavelengths 430 nm and 500 nm, respectively.

Further, the full width at half maximum (FWHM) of the emission spectrum of the light source can, for example, be below 50 nm, preferably below 30 nm.

The optical device according to the second aspect is advantageously realized as a pair of glasses worn by the user. The device thus offers a portable and discrete anti-somnolence solution. Thanks to the wavelength selection by the coating and the fact that the light is not irradiated directly from the light source into the user's eyes, the user is not glared by the device. The device may be personalized according to the needs and wishes of any user. Finally, thanks to the compactness and discretion of the device, it is also esthetic and may be worn continuously, for example by switching off the light source when unneeded and/or during the day.

According to a third aspect, there is provided a method for providing an anti-somnolence optical device, using the optical device according to the second aspect. The method comprises the following steps:

acquiring wearer's data representing physical features of the wearer, acquiring optical device data representing features of the optical device, and determining and enabling a position of the light source depending on the cooperation of the wearer's data and the optical device's data.

According to an embodiment, the light source position and orientation are adjusted with regard to the coating's position on the ophthalmic lens and to the coatings reflection properties.

Preferably, the light source is adjusted, regarding either or both of its intensity and the selectivity of its emission spectrum, with regard to respectively, either or both of the reflection value with the range of 460 nm to 480 nm, and the selectivity of the reflection spectrum.

In an embodiment, the light source and the coating of the invention cooperate to direct toward the pupil of the user, by reflection, a light beam with a spectral distribution comprising essentially a peak with a FWHM of less than or equal to 50 nm, preferably less than or equal to 30 nm, with highest intensity at a wavelength comprised between 460 nm and 480 nm, such that about 20 lux to 1000 lux, preferably 100 lux to 500 lux, for example 200 lux to 300 lux, of light with a wavelength comprised between 450 nm and 490 nm reaches the pupil.

Using this cooperation, each of the light source and the coating may compensate defects of the other element: for example, a broad-band light source may be compensated by a coating with a highly selective reflection spectrum, or vice-versa, or a low-reflection coating may be compensated by a light source emitting much light, or the shape of the coating, for example not covering part of the working optical zone, may compensate for a light-source having an illumination zone covering the working optical zone.

Additional aspects and advantages of systems, devices, and methods according to embodiments disclosed herein will be set forth in and be apparent from the detailed description, figures and any claims which follow.

BRIEF DESCRIPTION OF THE DRAWINGS

Exemplary embodiments of the present invention are described with reference to the accompanying drawings, in which.

DETAILED DESCRIPTION OF THE PREFERRED EMBODIMENTS

The figures and the following detailed description illustrate exemplary embodiments.

Figure 1:
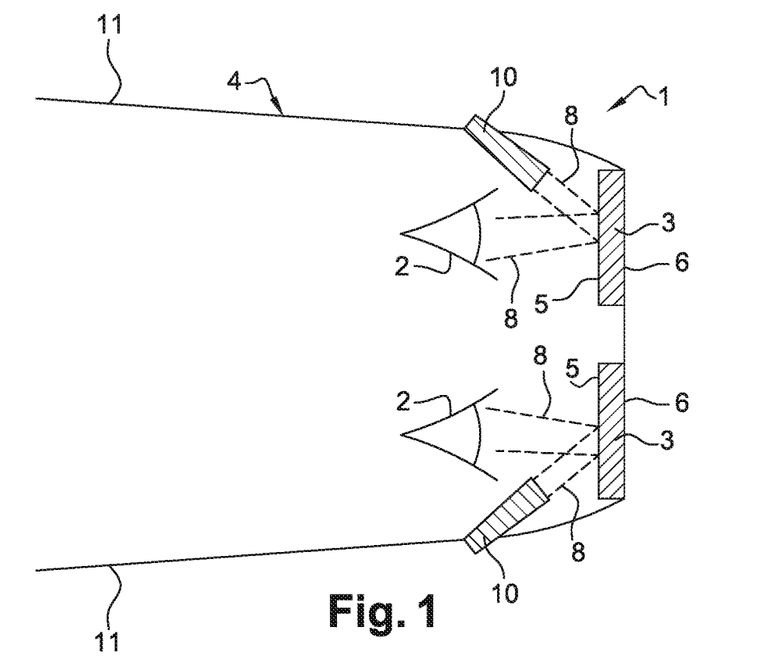
FIG. 1 schematically shows an ophthalmic device according to an embodiment.

Reference is made to FIG. 1, which shows an embodiment of an ophthalmic device according to the present invention. A pair of glasses 1, to be worn in front of a user's eyes 2, comprises two ophthalmic lenses 3 and a frame 4 supporting the lenses 3. The ophthalmic lenses 3 function as substrates for at least one coating applied on the rear side 5 of each lens 3. The lenses 3 may be correction glasses to counteract defaults of visual acuity of the user. The lenses 3 may also be simple glass plates destined only to support the coating. The lenses 3 may comprise one or more coatings on the substrate on the front side of the lens, such as any of an anti-shock coating, glue, a support coating, an anti-scratch coating, an antireflective stack, an anti-smudge coating, an anti-fog coating, an anti-static coating, a photochromic layer, a polarized layer, an active layer or any combination thereof.

Further, the lenses 3 may comprise one or more coatings on the substrate on the rear side of the lens, such as any of an anti-shock coating, a glue, a support coating, an anti-scratch coating, an anti-reflective stack, for example only on a part of the surface, an anti-smudge coating, an anti-fog coating, an anti-static coating, a photochromic layer or a tinted layer, a polarized layer, an active layer, or any combination thereof. The anti-smudge coating or anti-fog coating, if present, is generally present over the coating of the invention.

In the following examples, it is assumed that the interferential coating of the invention is on the rear face of the optical lens; therefore, coatings on the rear side of the lens are described. In alternative embodiments, the interferential coating of the invention is on the front face of the optical lens, or present on both faces. Accordingly, the description above and below applies mutatis mutandis to an interferential coating of the invention present on the front face of the optical lens.

Material for the substrates of the lenses 3 may include any thermoset or thermoplastic, homopolymers, co-polymers or blends, which are usually used in ophthalmic field. Mention may be made, by way of examples, of substrates made of polycarbonate, of polymethylmethacrylate, of polyamide, of polyimide, of polysulfone, of copolymers of poly(ethylene terephthalate) and polycarbonate, of polyolefins, in particular of polynorbornene, of homopolymers and copolymers of diethylene glycol bis(allyl carbonate), of (meth)acrylic polymers and copolymers, in particular (meth)acrylic polymers and copolymers derived from bisphenol A, of thio(meth)acrylic polymers and copolymers, of polyurethane and polythiourethane homopolymers or copolymers, epoxy polymers and copolymers and episulfide polymers and copolymers.

For example, it will be possible to use a diethylene glycol bis(allyl carbonate), such as CR39®, in particular with a refractive index of 1.5, sold by PPG Industries, or else a polythiourethane, such as MR7®, in particular with a refractive index of 1.66, sold by Mitsui.

Figure 2:
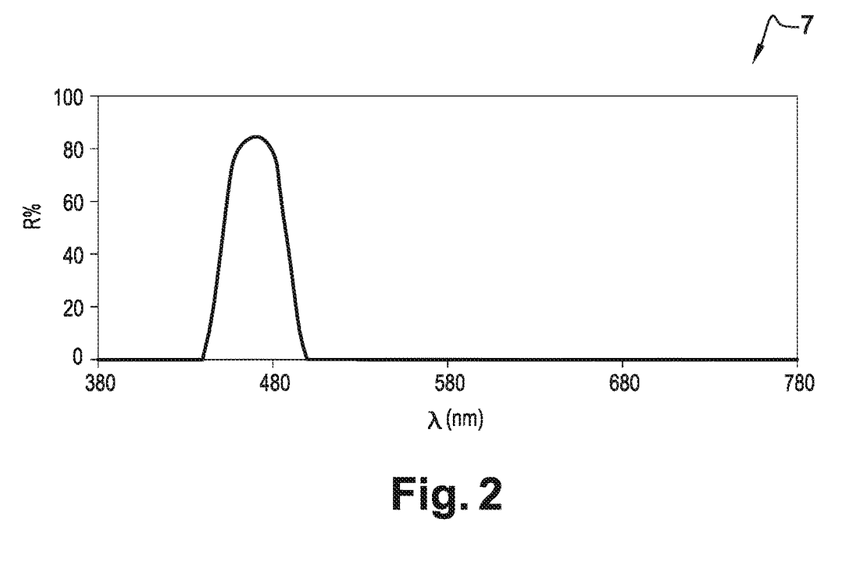
FIG. 2 shows an expected reflection spectrum of an ophthalmic lens according to an embodiment.

The coating applied to the rear face 5 of the lenses 3 is designed such that light incident onto the rear face 5 of the lenses 3 and of which the wavelength is centered around 470 nm is selectively reflected, and the remaining wavelengths of the visible spectrum are absorbed. A wavelength of approximately 470 nm is considered to be the most appropriate to perturb the circadian rhythm of the user, while not being harmful to him. An expected reflection spectrum 7 of such a coating is shown in FIG. 2, tracing the reflectivity R in % of the coating over the wavelength $\lambda$ in nm of the incident light. The coating thus combines the function of a partial optical mirror within the 450 nm-470 nm range with that of an anti-reflection (AR) coating for at least some parts of the visual spectrum out of the 450 nm-470 nm range. The coating is also designed such that the amount of reflected light is controlled in order to avoid glaring of the user. In an embodiment, the coating of the invention is an interferential coating.

Examples of the coating and their physical properties will be detailed more thoroughly below.

A conventional anti-reflection coating may also be applied to the front face 6 of the lenses 3.

Still referring to FIG. 1, the pair of glasses 1 further comprises two light sources 10. Preferably, the light sources 10 are light-emitting diodes (LED) 10. LEDs are small and lightweight and may thus be easily integrated with an eyeglass frame. The head of such a LED measures, for example, less than 10 mm in length. In the embodiment shown in FIG. 1, the LEDs 10 are mounted on the temples 11 of the frame of the eyeglasses 1. The LEDs 10 are mounted such that the light emitted by them is directed onto the rear faces 5 of the lenses 3. From the rear faces 5 of the lenses 3, the light is reflected into the user's eyes 2. The light rays are schematized by dashed lines 8. In a particular embodiment, the LEDs 10 employed in the device 1 according to the invention emit light of which the wavelength spectrum is centered around the desired blue wavelength, i.e., around 470 nm. The LEDs 10 are connected to resistances. The LEDs 10 may be powered by batteries, for example flat 9V batteries.

In the embodiment described above, the LEDs 10 are arranged with respect to the lenses 3 such that the lenses are irradiated by the LEDs 10 outside of a working optical zone of the lens, which is as defined above, such as not to perturb the vision of the user. Preferably, the lenses 3 are irradiated outside of their working optical zone on the temple side.

Alternatively, only a part of the working optical zone of the lens is irradiated.

The working optical zone of a lens 3 is defined as a region of the lens surface through which the user is viewing during a particular viewing task, for a conventional usage or a given distance. In particular, it is defined as a zone comprising at least 75%, preferentially 80%, preferentially 90% of the intersection points weighed by time spent per unit area for a given user, using the definitions as defined here above. The working optical zone may be described as a statistical distribution of points on the lens surface or another projection surface, or as a statistical distribution of vectors representing the viewing directions of the user. Alternatively, the working optical zone may also be defined by a statistical distribution of declining viewing angles in the sagittal plane of the user.

While the working optical zone highly depends on the user's visual behavior, the working optical zone is generally greater than a circle of radius of 7 mm, centered on the optical center of the lens, and rarely extends out of a circle of 18 mm, centered on the optical center of the lens.

Accordingly, the working optical zone is generally described as a circle or ellipse centered on the optical center of the lens and of radius comprised between 7 mm and 18 mm.

In one embodiment, in order to have the illumination zone be mostly out of the working optical zone, the orientation and positioning of the light source is precisely defined: indeed, for a LED having a spatial emission angle of approximately 30°, it can be positioned with an arrangement of the LED on the temple at approximately 10-30 mm from the lens, an orientation of the LED in the horizontal plane of approximately 20-40° in the direction of the nose of the user and in the vertical plane of approximately 5-15° downwards. In such case, it is possible to irradiate the lens outside its working optical zone for most users and frames while still having the lens reflecting the light emitted from the LED into the pupil of the user. The orientation and arrangement of the LED may be further adjusted manually individually for every user.

In a first mounting embodiment of the invention, for a given frame, a LED, having a 30° emission cone, is placed on the arm of the frame back of approximately 20 mm from the lens, the lens is oriented in the horizontal plane at an angle of 30° towards the nose and in the vertical plane at an angle of 10° downward. This embodiment enables, for a given frame, a reflection of the rays toward the pupil of the eye, while illuminating the lens essentially outside the working optical zone, on the temporal side of the lens, to avoid disturbing the wearer, for a wide range of curvatures of the back of the lens (radii between 95 and 160 mm).

Figure 3A:
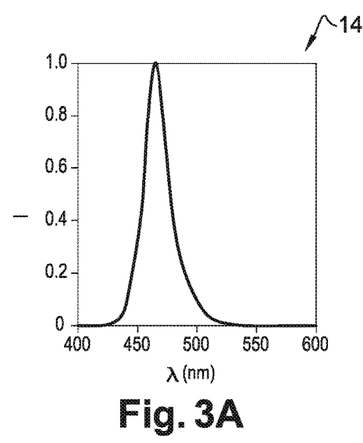
FIGS. 3A and 3B represent an intensity spectrum and a spatial distribution diagram, respectively, of a light emitting diode used with the ophthalmic device according to an embodiment.
Figure 3B:
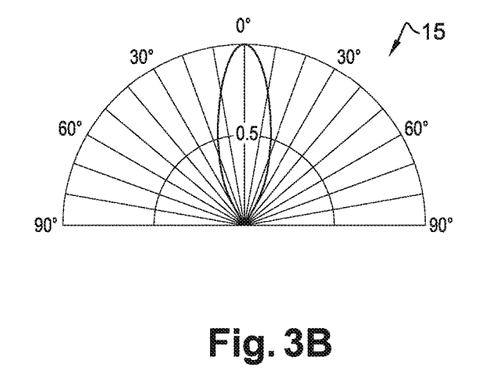

As an example, LEDs of the type UB5305S of the Stanley company may be used. These LEDs emit selectively a light of wavelengths centred on 470 nm. The emission spectrum 14 of such a diode is shown in FIG. 3A, where the relative intensity I is plotted over the wavelength $\lambda$ in nm. The emitted intensity in the harmful range of 420-450 nm is much weaker than that at the desired wavelength of around 470 nm, by a factor of about 5 to 10. FIG. 3B shows an example of the spatial distribution 15 of emitted light of such a LED in the half-space as a function of the emission angle in degree. Other LEDs that have an emission of light in the 460 nm-480 nm range can be used, even with a broader FWHM.

A first exemplified LED, of the type UB5305S, has an emitted intensity of 1 candela, a FWHM of 25 nm to 30 nm, and a 30° emission cone.

In the following, the implementation of the coating of the invention applied on the rear face of the lenses is described in more detail with regard to embodiments of the coating as an interferential coating. The optical design of the interferential coating implies a specific stack of layers of different materials such that the desired reflection properties as mentioned above will be obtained.

It is to be noted that the following example are related to the interferential coating of the invention, but as mentioned above, the rear face may comprise in the working optical zone a rear antireflective stack which do not need to have the properties of the interferential coating of the invention. The rear antireflective stack may be the rearest coating on the whole working optical zone, or only a portion of it, for example a circle or ellipse of radius comprised between 7 mm included and 18 mm included centered on the optical center of the lens.

The rear antireflective stack may be positioned side by side with the interferential coating of the invention, or, it may be apparent in part of the working optical zone, and positioned under at least some layers of the interferential coating of the invention. In that second case, the interferential coating of the invention is made, out of the zone where the antireflective stack is apparent, by adding layers of HI and LI materials on top of the antireflective stack.

In the following two examples, the interferential coating is composed of a stack of 8 layers of alternating HI and LI layers. The HI layer is a tantalum pentoxide ($Ta_2O_5$) layer, and the LI layer is a silicon oxide ($SiO_2$) layer. The reflection spectra for both examples are simulated using a ray tracing software.

The stack consists of layers of high refractive index (HI) and layers of low refractive index (LI). The number of layers used for the stack depends on the desired interferential functions of the coating. The maximum reflection in the embodiment is situated around 470 nm. It is chosen to have a narrow reflection peak, i.e., a high selectivity, at this wavelength. The reflection of the other parts of the visible spectrum is to be minimized. The number of layers is not limited. The selectivity of the interferential function can be increased by increasing the number of layers. The number of layers and their thickness is also determined by the refractive indices of the materials used.

Figure 4A:
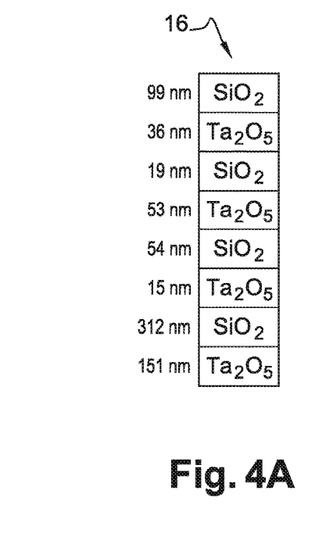
FIGS. 4A and 4B show a first example of a coating of the ophthalmic lens according to an embodiment and a reflection spectrum of the coating, respectively.
Figure 4B:
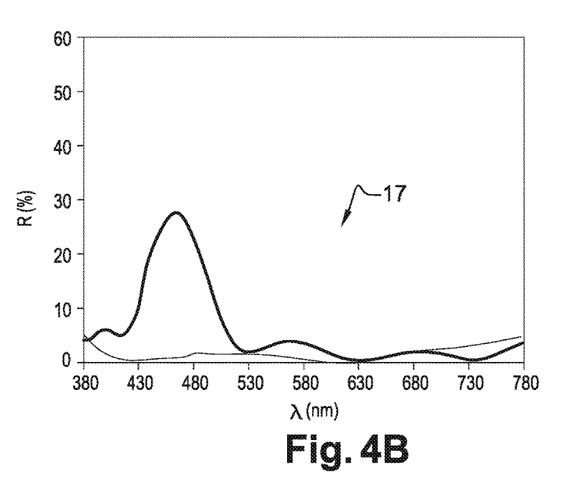
Figure 5A:
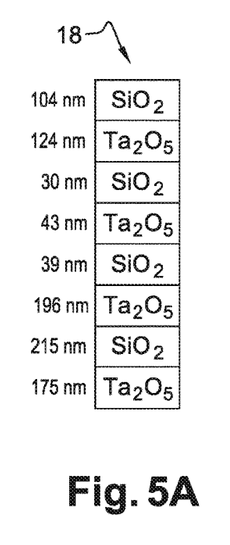
FIGS. 5A and 5B show a second example of a coating of the ophthalmic lens according to an embodiment and a reflection spectrum of the coating, respectively.
Figure 5B:
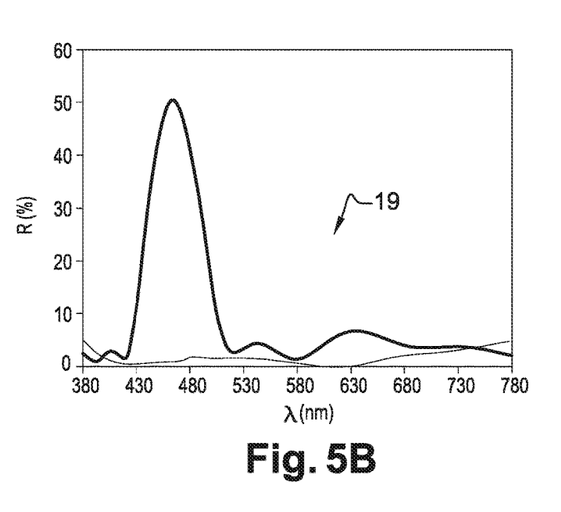

FIG. 4A and FIG. 5A show two examples of structures of interferential coatings of the invention: a first interferential stack 16 and a second interferential stack 18, respectively. In both stacks 16, 18, the alternating $Ta_2O_5$ and $SiO_2$ layers have different thicknesses varying between 15 nm and 312 nm, as shown in FIGS. 4A and 5A. FIGS. 4B and 5B represent the calculated reflection spectra 17, 19 for the two stack examples 16, 18, respectively as if reflecting natural white light. The reflection spectra 17, 19 are traced for the whole visible wavelength range. Depending on the choice of the thicknesses of the different layers and their arrangement with respect to each other, the reflectivity of the stack can be adjusted such that the reflectivity peak around 470 nm is more or less narrow. For the second example stack 18, the reflectivity 19 shows a pronounced peak at 470 nm of around 50%, whereas for the first example stack 16, the reflectivity 17 at 470 nm is less than 30%, namely approximately 27%. Also, the second example stack 18 is more selective at the desired wavelength of 470 nm. For both example stacks, an interferential function akin to an AR function in the visible range is existing beyond the wavelength range of approximately 430 nm-510 nm. In the first example (FIG. 4B), the mean reflectivity in the ranges of 380 nm-430 nm and 510 nm-780 nm is approximately 1.9%. In the second example (FIG. 5B), the mean reflectivity in the ranges of 380 nm-430 nm and 510 nm-780 nm is approximately 3%.

Figure 6A:
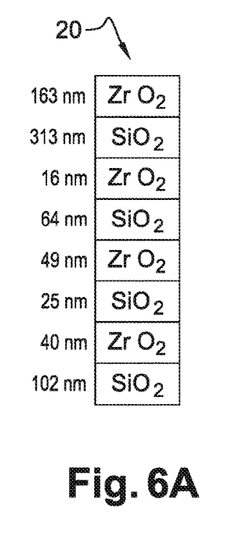
FIGS. 6A and 6B show a third example of a coating of the ophthalmic lens according to an embodiment and a reflection spectrum of the coating, respectively.
Figure 6B:
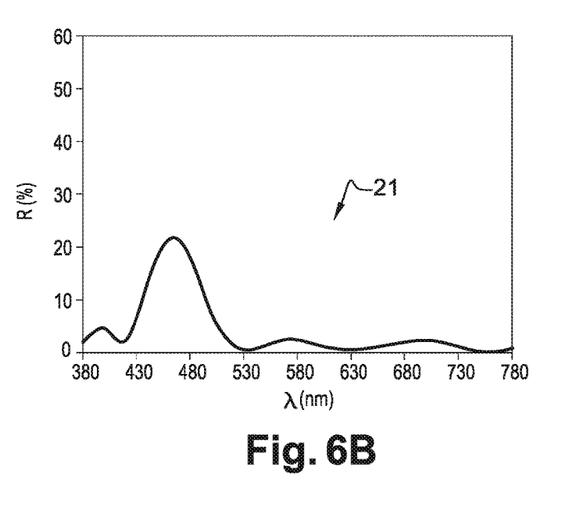

FIG. 6A shows one example of a third interferential stack 20 in which the alternating $ZrO_2$ and $SiO_2$ layers have different thicknesses varying between 16 nm and 313 nm, whereby the $SiO_2$ are the LI layers and the $ZrO_2$ layers are the HI layers. FIG. 6B represents the calculated reflection spectra 21 for the stack example 20 as if reflecting natural white light. The reflection spectrum 21 is traced for the whole visible wavelength range. Depending on the choice of the thicknesses of the different layers and their arrangement with respect to each other, the reflectivity of the stack can be adjusted such that the reflectivity peak around 470 nm is more or less narrow. The reflectivity 21 shows a pronounced peak at 470 nm of around 20% and this stack exhibits the interferential function in the visible range in the wavelength range of approximately 430 nm-510 nm. The mean reflectivity in the ranges of 380 nm-430 nm and 510 nm-780 nm is approximately 1.6%.

Thus in those examples, the interferential stack has around the 470 nm wavelength a reflectivity of about 20% or greater.

Such third interferential stack, present on a lens of the first mounting embodiment, using the first example LED, enables to direct 200 lux to 300 lux of light of wavelength between 450 nm and 490 nm toward the pupil of the user, with most of the illumination from the LED being outside of the working optical zone.

It is possible to adjust the design of the stacks in order to decrease the reflectivity in the blue wavelength region so as not to reflect too much light to the user which could bedazzle the user. The dazzling of the user is not evaluable as an absolute value, but only individually and empirically, for example using a de-Boer scale. The impression of annoyance depends on the spectral range of the light and exterior lighting conditions, such as strong sunlight. However, according to an article in Ophthal. Physiol. Opt. 2010 30: 182-187, the human eye is less sensitive to glare in the blue region of the visible spectrum, and thus less prone to be dazzled by light of this wavelength range.

It is further possible to adjust the emission intensity of the LEDs used in the device according to the invention. For example, the intensity may be adjusted as a function of the age, potential usage conditions, personnel sensitivity, etc. of the intended user. For this, the de Boer scale, may be used. The de Boer scale is well known by the person skilled in the art as a mean to evaluate discomfort brought by glare by measuring the subjective visual comfort in case of glare and ranging from 1 ("unbearable") to 9 ("unnoticeable"). For example, the subjective glare impression may be limited to a minimum of 7 ("satisfactory").

According to another embodiment, LEDs emitting a large spectrum may be used. In this case, according to the invention it is preferable that the interferential function of the coating on the rear faces of the lenses is optimized such as to have a high reflectivity at approximately 470 nm and a low reflectivity at the other wavelengths. In order to achieve such a reflectivity spectrum with a broad-spectrum LED, the number of layers of the coating may be higher than 8.

Alternatively, according to yet another embodiment, a coating reflecting light in a broad spectrum may be used. In this case, according to the invention, it is preferable that the LED is chosen such as to have a high selectivity of light emitted, with a wavelength emission peak close to 470 nm.

In particular, as a larger-band reflectivity spectrum is allowed for the interferential coating, the number of layers of the coating may be lower than 8.

Alternatively, according to yet another embodiment, a coating reflecting light with a reflection peak at a wavelength smaller than 470 nm may be used in conjunction with a LED chosen such as to have a high selectivity of light emitted, with a wavelength emission peak at a wavelength greater than 470 nm. The spectrum selectivity and peak wavelength are preferably chosen so that the combination of the two elements, LED and coating, enable to have a reflected light with a reflected spectrum having a peak close to 470 nm.

Some radiation of the blue spectrum, more precisely with a wavelength in the range of approximately 420 nm-450 nm, especially of about 435 nm, sometimes considered to be phototoxic. In an embodiment, the light source and the coating of the invention cooperate so as to minimize the amount of light of the 420-450 nm range reflected toward the pupil of the user.

For example, the blue LED mentioned above (of the type UB5305S of the Stanley company) emits selectively around 470 nm (relative intensity=1, see FIG. 3A). The emission in the phototoxic region is relatively weak, with a relative intensity of 0.25 at 450 nm and of 0.05 at 430 nm (see FIG. 3A). If such a LED is combined with a coating made of the first example interferential stack described above, it is possible to obtain a reflectivity ratio of the light reflected with a wavelength of 470 nm to that of 430 nm of 50. In case of using a coating made of the second example interferential stack described above, the reflectivity ratio is of about 200. In case of using a coating made of the third example interferential stack, the reflectivity ratio is close to 90.

The invention claimed is:

1. An optical device, comprising:
   an ophthalmic lens, said ophthalmic lens comprising
      a substrate, the substrate having a rear face and a front face, the rear face being destined to face the eye of a user, and
      at least one external interferential coating on at least one face, the at least one interferential coating being such that it enables to selectively reflect light arriving on the rear face with a local maximum of reflection of at least 10% for a wavelength within the range between 450 nm and 490 nm;
   a frame for supporting the ophthalmic lens in front of a wearer's eye; and
   a light source attached to the frame, the light source being positioned and oriented for emitting a light toward the interferential coating, such that the light does not illuminate directly the eye and such that the light emitted by the light source is reflected at least partially by the interferential coating toward the eye.

2. The optical device according to claim 1, in which the mean reflection for light in the range between 420 nm and 440 nm is less than 10%.

3. The optical device according to claim 1, in which a reflection spectrum of the interferential coating comprises a peak centered between 450 nm and 490 nm, the peak having a full width at half maximum, FWHM, smaller or equal to 100 nm.

4. The optical device according to claim 1, in which the coating comprises layers of high refractive index, HI, and layers of low refractive index, LI, said layers each having a thickness within the range of 1 nm to 500 nm, and each of the LI layers of the coating comprises one oxide selected from the group consisting in silicon oxide, magnesium fluoride, $MgF_2$, $ZrF_4AlF_3$, chiolite, $Na_3[Al_3F_{14}]$, cryolite, $Na_3[AlF_6]$, and their combinations, combined with higher index materials comprising alumina ($Al_2O_3$), fluorine, silicon dioxide, $SiO_2$ or $SiO_2$ doped with alumina, and each of the HI layers of the coating comprises one or more metal oxides which are selected from the group comprising zirconia, titanium dioxide, $TiO_2$, alumina, $Al_2O_3$, tantalum pentoxide, $Ta_2O_5$, neodymium pentoxide, $Nd_2O_5$, praseodymium oxide, Pr2O3, praseodymium titanate oxide, $PrTiO_3$, lanthanum oxide, $La_2O_3$, niobium oxide, $Nb_2O_5$, yttrium oxide, $Y_2O_3$.

5. The optical device according to claim 1, the interferential coating being present on the rear face of the lens.

6. The optical device according to claim 1, the light source emitting with a spectrum with a maximum of emission for a wavelength within the range of 460 nm to 480 nm, with a full width half maximum, FWHM, of less than 50 nm.

7. The optical device according to claim 1, the light source and the interferential coating cooperating to direct toward the pupil of the wearer, by reflection, a light beam with a spectral distribution comprising a peak with a FWHM of less than or equal to 50 nm, with highest intensity at a wavelength comprised between 460 nm and 480 nm, such that about 20 lux to 1000 lux reaches the pupil.

8. The optical device according to claim 1, in which the light source is positioned and oriented for having an illumination area, representing an area receiving 80% of the intensity of the light emitted by the light source as it intersects a surface of the coating on the rear face of the substrate, outside a working optical zone of the lens surface.

9. The optical device according to claim 1, the light source and the interferential coating cooperating to direct toward the pupil of the wearer, by reflection, a light beam with a spectral distribution comprising a peak with a FWHM of less than or equal to 30 nm, with highest intensity at a wavelength comprised between 460 nm and 480 nm, such that about 200 lux to 300 lux of light with a wavelength comprised between 450 nm and 490 nm reaches the pupil.

10. The optical device according to claim 1, in which the mean reflection for light in the range between 400 nm and 420 nm is less than 10% and/or the mean reflection for light in the range between 500 nm and 600 nm is less than 10%.

11. The ophthalmic lens according to claim 10 in which the coating comprises layers of high refractive index, HI, and layers of low refractive index, LI, said layers each having a thickness within the range of 1 nm to 500 nm, and each of the LI layers of the coating comprises one oxide selected from the group consisting in silicon oxide, magnesium fluoride, $MgF_2$, $ZrF_4AlF_3$, chiolite, $Na_3[Al_3F_{14}]$, cryolite, $Na_3[AlF_6]$, and their combinations, combined with higher index materials comprising alumina ($Al_2O_3$), fluorine, silicon dioxide, $SiO_2$ or $SiO_2$ doped with alumina, and each of the HI layers of the coating comprises one or more metal oxides which are selected from the group comprising zirconia, titanium dioxide, $TiO_2$, alumina, $Al_2O_3$, tantalum pentoxide, $Ta_2O_5$, neodymium pentoxide, $Nd_2O_5$, praseodymium oxide, Pr2O3, praseodymium titanate oxide, $PrTiO_3$, lanthanum oxide, $La_2O_3$, niobium oxide, $Nb_2O_5$, yttrium oxide, $Y_2O_3$.

12. The optical device according to claim 1, in which the local maximum of reflection within the range between 450 nm and 490 nm has a reflection value of at least two times greater than the reflection value of light of wavelength 430 nm and/or of light of wavelength 500 nm.

13. The optical device according to claim 12, wherein the local maximum of reflection within the range between 450 nm and 490 nm has a reflection value of at least four times greater than the reflection value of light of wavelength 430 nm and/or of light of wavelength 500 nm.

14. The optical device according to claim 1, in which the coating is not present on the entire surface of the face of the substrate it is positioned on.

15. The optical device according to claim 14, the interferential coating being absent from part of a working optical zone of the lens.

16. The optical device according to claim 1, in which the light source is positioned and oriented for having an illumination area, representing an area receiving 60% of the intensity of the light emitted by the light source as it intersects a surface of the coating on the rear face of the substrate, outside a working optical zone of the lens surface.

17. The optical device according to claim 16, the light source emitting with a spectrum with a maximum of emission for a wavelength within the range of 460 nm to 480 nm, with a full width half maximum, FWHM, of less than 50 nm.

18. A method for providing an anti-somnolence optical device, comprising the following steps:
   providing an optical device that includes
      an ophthalmic lens, said ophthalmic lens comprising a substrate, the substrate having a rear face and a front face, the rear face being destined to face the eye of a user, and at least one external interferential coating on at least one face, the at least one interferential coating being such that it enables to selectively reflect light arriving on the rear face with a local maximum of reflection of at least 10% for a wavelength within the range between 450 nm and 490 nm,
      a frame for supporting the ophthalmic lens in front of a wearer's eye, and
      a light source attached to the frame, the light source being positioned and oriented for emitting a light toward the interferential coating, such that the light does not illuminate directly the eye and such that the light emitted by the light source is reflected at least partially by the interferential coating toward the eye;
   acquiring wearer's data representing physical features of the wearer;
   acquiring optical device data representing features of the optical device; and
   determining and enabling a position of the light source depending on the cooperation of the wearer's data and the optical device's data.

19. The method according to 18, wherein the light source position and orientation are adjusted with regard to the coating's position on the ophthalmic lens and to the coatings' reflection properties.

20. The method according to claim 19, wherein the light source is adjusted, regarding either or both of its intensity and the selectivity of its emission spectrum, with regard to respectively either or both of the reflection value R % with the range of 460 nm to 480 nm and the selectivity of the reflection spectrum.

* * * * *